US010939852B2

(12) United States Patent
Guazzi et al.

(10) Patent No.: US 10,939,852 B2
(45) Date of Patent: Mar. 9, 2021

(54) METHOD AND APPARATUS FOR VITAL SIGNS MEASUREMENT

(71) Applicant: OXFORD UNIVERSITY INNOVATION LIMITED, Botley (GB)

(72) Inventors: Alessandro Guazzi, Oxford (GB); Mauricio Villarroel Montoya, Oxford (GB); Lionel Tarassenko, Oxford (GB)

(73) Assignee: OXFORD UNIVERSITY INNOVATION LIMITED, Botley (GB)

( * ) Notice: Subject to any disclaimer, the term of this patent is extended or adjusted under 35 U.S.C. 154(b) by 273 days.

(21) Appl. No.: 15/579,653

(22) PCT Filed: Jun. 2, 2016

(86) PCT No.: PCT/GB2016/051628
§ 371 (c)(1),
(2) Date: Dec. 5, 2017

(87) PCT Pub. No.: WO2016/193735
PCT Pub. Date: Dec. 8, 2016

(65) Prior Publication Data
US 2018/0153455 A1 Jun. 7, 2018

(30) Foreign Application Priority Data
Jun. 5, 2015 (GB) .................................. 1509809.8

(51) Int. Cl.
*A61B 5/1455* (2006.01)
*A61B 5/00* (2006.01)
(Continued)

(52) U.S. Cl.
CPC ........ *A61B 5/14551* (2013.01); *A61B 5/0077* (2013.01); *A61B 5/02416* (2013.01);
(Continued)

(58) Field of Classification Search
None
See application file for complete search history.

(56) References Cited

U.S. PATENT DOCUMENTS

| 2006/0206019 A1 | 9/2006 | Zhang et al. |
| 2014/0276089 A1 | 9/2014 | Kirenko et al. |
| 2014/0303454 A1 | 10/2014 | Clifton et al. |

FOREIGN PATENT DOCUMENTS

| WO | WO-2013/027027 A2 | 2/2013 |
| WO | WO-2015/055405 A1 | 4/2015 |

OTHER PUBLICATIONS

J. W. Severinghaus. "Takuo Aoyagi: Discovery of Pulse Oximetry." Anesthesia & Analgesia, vol. 105, No. 6. International Anesthesia Research Society. Dec. 2007.
(Continued)

*Primary Examiner* — Marjan Fardanesh
(74) *Attorney, Agent, or Firm* — Harness, Dickey & Pierce, P.L.C.

(57) ABSTRACT

A method of monitoring changes in oxygen saturation of a subject by analysing a three colour channel video image of the exposed skin of the subject. Within each colour channel a normalised signal obtained by dividing the intensity signal by its mean value, and the normalised signals are averaged across plural regions of interest within the exposed skin area image of the subject. Regions of interest are selected on the basis of the signal-to-noise ratios for the heart rate and breathing rate components. A single representative waveform for each colour channel is obtained by signal averaging and the ratio of the amplitudes of the representative waveforms from two different colour channels, e.g. blue and red, is taken. The changes in the ratio of amplitudes is output as a measure of changes in blood oxygen saturation.

15 Claims, 3 Drawing Sheets

Figure 1:
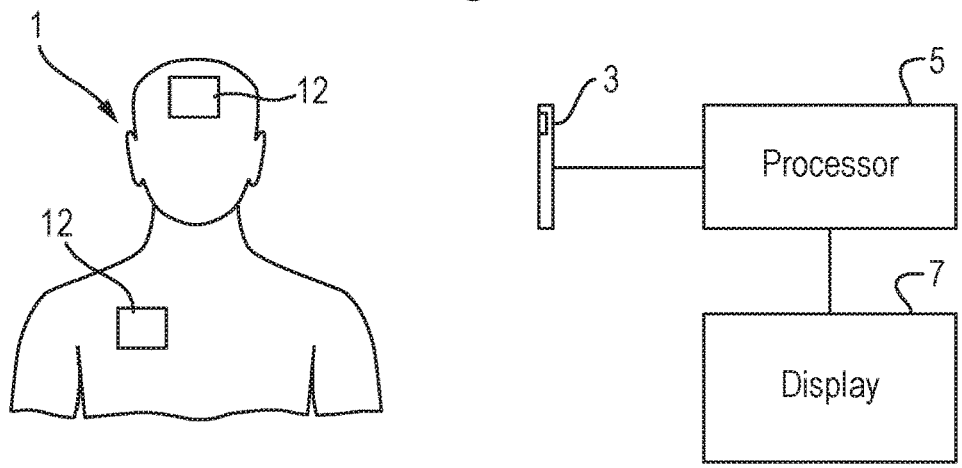

(51) Int. Cl.
    A61B 5/024    (2006.01)
    G06T 7/00     (2017.01)
    A61B 5/08     (2006.01)
(52) U.S. Cl.
    CPC .......... *G06T 7/0012* (2013.01); *A61B 5/0816* (2013.01); *A61B 5/7221* (2013.01); *A61B 5/7257* (2013.01); *G06T 2207/30076* (2013.01); *G06T 2207/30104* (2013.01)

(56) References Cited

OTHER PUBLICATIONS

C. D. Hanning and J. M. Alexander-Williams. "Pulse Oximetry: A Practical Review." BMJ: British Medical Journal, vol. 311, No. 7001. Aug. 5, 1995. pp. 367-370.
F.P. Wieringa et al. "Contactless Multiple Wavelength Photoplethysmographic Imaging: A First Step Toward "SPO2 Camera" Technology." Annals of Biomedical Engineering, vol. 33, No. 8. Aug. 2005. pp. 1034-1041.
G. de Haan and A. van Leest. "Improved motion robustness of remote-PPG by using the blood volume pulse signature." Physiological Measurement, vol. 35, No. 9. Aug. 27, 2014. Institute of Physics and Engineering in Medicine. pp. 1913-1926.
F. Bousefsaf et al. "Continuous wavelet filtering on webcam photoplethysmographic signals to remotely assess the instantaneous heart rate." Biomedical Signal Processing and Control, vol. 8, Issue 6. Nov. 2013. pp. 568-574.
W. Verkruysse et al. "Remote plethysmographic imaging using ambient light." Optics Express, vol. 16, No. 26. Optical Society of America. Dec. 12, 2008.
M. Z. Poh et al. "Non-contact, automated cardiac pulse measurements using video imaging and blind source separation." Optics Express, vol. 18, No. 10. Optical Society of America. May 7, 2010.
M. C. Wilkins. "Residual bacterial contamination on reusable pulse oximetry sensors." Respiratory Care. Nov. 1, 1993. Abstract only.
D. A. Benaron et al. "Continuous, noninvasive, and localized microvascular tissue oximetry using visible light spectroscopy." Anesthesiology. Jun. 2004. Abstract only.
I. Nishidate et al. "Visualizing of skin chromophore concentrations by use of RGB images." Optics Letters, vol. 33, No. 19. Sep. 30, 2008. Optical Society of America. pp. 2263-2265.
L. Kong et al.. "Non-contact detection of oxygen saturation based on visible light imaging device using ambient light." Optics Express, vol. 21, No. 15. Jul. 15, 2013.
C. G. Scully et al. "Physiological Parameter Monitoring from Optical Recordings With a Mobile Phone." IEEE Transactions on Biomedical Engineering, vol. 59, No. 2. Jan. 20, 2012. pp. 303-306.
L. Tarassenko et al. "Non-contact video-based vital sign monitoring using ambient light and auto-regressive models." Physiological Measurement. Institute of Physics and Engineering in Medicine. Mar. 28, 2014. pp. 807-831.
M. Villarroel et al. "Continuous non-contact vital sign monitoring in neonatal intensive care unit." Healthcare Technology Letters, vol. 1, Issue 3. Sep. 18, 2014. pp. 87-91.
M. Kumar et al. "DistancePPG: Robust non-contact vital signs monitoring using a camera." Biomedical Optics Express, vol. 6, No. 5. Optical Society of America. Apr. 6, 2015.
G. Balakrishnan et al. "Detecting Pulse from Head Motions in Video." Proceedings of the 2013 IEEE Conference on Computer Vision and Pattern Recognition. Jun. 23-28, 2013.
Q. J. W. Milner and G. R. Matthews. "An assessment of the accuracy of pulse oximeters." Anaesthesia. The Association of Anaesthetists of Great Britain and Ireland. Feb. 11, 2012.
L. S. Howard et al. "Chamber for controlling end-tidal gas tensions over sustained periods in humans." Journal of Applied Physiology, vol. 78, Issue 3. The American Physiological Society. Mar. 1, 1995. pp. 1088-1091.
R. K. Pearson. "Outliers in Process Modeling and Identification." IEEE Transactions on Control Systems Technology, vol. 10, No. 1. Jan. 2002. pp. 55-63.
G. Zonios et al. "Skin Melanin, Hemoglobin, and Light Scattering Properties can be Quantitatively Assessed in Vivo Using Diffuse Reflectance Spectroscopy." The Journal of Investigative Dermatology, vol. 117, No. 6. The Society for Investigative Dermatology, Inc. Dec. 2001. pp. 1452-1457.
B. R. O'Driscoll et al. "BTS guideline for emergency oxygen use in adult patients." Thorax, vol. 63, Issue Supplement 6. Oct. 6, 2008.
B. D. Kent et al. "Hypoxemia in patients with COPD: cause, effects, and disease progression." International Journal of COPD, vol. 6. Mar. 14, 2011. pp. 199-208.
K. F. Palmer and D. Williams. "Optical properties of water in the near infrared*." Journal of the Optical Society of America, vol. 64, No. 8. Aug. 1974. pp. 1107-1110.
U. Bal. "Non-contact estimation of heart rate and oxygen saturation using ambient light." Biomedical Optics Express, vol. 6, No. 1. Optical Society of America. Dec. 10, 2014.
Y. Mendelson and J. C. Kent. "Variations in Optical Absorption Spectra of Adult and Fetal Hemoglobins and Its Effect on Pulse Oximetry." IEEE Transactions on Biomedical Engineering, vol. 36, No. 8. Aug. 1989. pp. 844-848.
I. Fine and A. Weinreb. "Multiple scattering effect in transmission pulse oximetry." Medical and Biological Engineering and Computing, vol. 33, Issue 5. Sep. 1995. pp. 709-712.
W. Karlen et al. "Design Challenges for Camera Oximetry on a Mobile Phone," In Proceedings of IEEE Engineering in Medicine and Biology Society Annual Conference. Aug. 28-Sep. 1, 2012. pp. 2448-2451.
J. Allen. "Photoplethysmography and its application in clinical physiological measurement." Physiological Measurement. Feb. 20, 2007.
B. Kaur et al. "Remotely Detected Differential Pulse Transmit Time as a Stress Indicator." Proceedings SPIE, vol. 9496. Jun. 2, 2015.
T. Fitzpatrick. "Soleil et peau." 1975.
Luis F. Corral Martinez et al: "Optimal wavelength selection for noncontact reflection photoplethysmography", Biomedical Photonics and Optoelectronic Imaging: Nov. 8-10, 2000, Beijing, China, vol. 8011, Aug. 15, 2011 (Aug. 15, 2011), pp. 801191-801191-7, XP055262353, Bellingham, Wash., US DOI:10.1117/12,903190; ISBN: 978-1-62841-832-3.
International Search Report and Written Opinion of the ISA for PCT/GB2016/051628, ISA/EP, Rijswijk, NL, dated Sep. 2, 2016.
Search Report under Section 17(5) for GB 1509809.8, IPO/UK, dated Nov. 11, 2015.

METHOD AND APPARATUS FOR VITAL SIGNS MEASUREMENT

CROSS-REFERENCE TO RELATED APPLICATIONS

This application is a 371 U.S. National Stage of International Application No. PCT/GB2016/051628, filed Jun. 2, 2016, which claims the benefit of British Patent Application No. 1509809.8, filed Jun. 5, 2015. The entire disclosures of the above applications are incorporated herein by reference.

The present invention relates to a method and apparatus for vital signs measurement and in particular to the estimation of blood oxygen saturation of a subject.

The measurement of vital signs such as heart rate, breathing rate and blood oxygen saturation is of critical importance in the medical field, but also finds application in other fields such as sports performance monitoring. Traditionally such vital signs have been measured by sensors placed in contact with the subject but more recently significant interest has developed in non-contact vital signs monitoring. In particular, the ready availability of reasonably high quality video cameras and their provision in many common devices such as tablet computers and smartphones has prompted efforts to derive measurements of vital signs such as heart rate and breathing rate from a video image of the exposed skin of a subject. WO-A2-2013/027027, for example, discloses deriving measurements of the heart rate and breathing rate from a photoplethysmographic image (PPGi) formed by the remote reflectance photoplethysmography (rPPG) signal. The rPPG signal is a variation in reflectance of light at certain wavelengths as the volume of blood in the skin capillaries varies with the cardiac cycle. Although invisible to normal sight, the skin can effectively be regarded as pulsing more red and less red with each heat beat. This change can be detected in the standard RGB colour video image of the skin taken with a normal video camera such as a webcam.

Blood oxygen saturation (SpO2), is a measure of the relative concentration of oxygenated haemoglobin in the blood with respect to the total haemoglobin. As a result, oxygen saturation is a very powerful measure for the assessment of lung function and the respiratory system itself. The clinical gold standard for precise measurement of oxygen saturation involves invasive blood gas analysis, but this has largely been supplanted by pulse oximetry which is the current standard for SpO2 measurement. Pulse oximetry takes advantage of the facts that: oxygenated haemoglobin and deoxygenated haemoglobin absorb differently at different wavelengths, that arterial blood is mostly pulsatile in nature, and that an optical window exists in the far visible and short-wave infrared in water. These factors allow SpO2 to be measured by illuminating tissue using red and infrared LED light sources in contact with the skin, measuring the reflected light intensity, and calculating the amplitude of the pulsatile component (AC) with respect to the baseline (DC) for both light sources. A ratio of ratios is then evaluated, usually the ratio of AC to DC in the red channel divided by the ratio of AC to DC in the infrared channel. This ratio of ratios is correlated to the blood oxygen saturation and can be converted into a measurement of SpO2 using a look-up table.

Although it has been recognised that the spatially-averaged RGB colour of skin in a PPGi video signal is correlated with arterial oxygen saturation, obtaining a reliable measurement of oxygen saturation, or even of the change in oxygen saturation, has not been possible because of the number of confounding factors and sources of noise. For example, the video signal can be affected by specular reflections from the skin of the subject (specularly reflected light not having interacted with the tissue of the subject), and any change in the geometrical alignment of the camera, skin and light source (such as, for example, a slight movement or change in orientation of the subject) causes changes in the video signal which are not related to changes in blood oxygen saturation. Changes in intensity of the ambient light also affect the signal. For this reason non-contact PPGi methods of vital signs monitoring have concentrated on obtaining better estimates of heart rate and breathing rate.

The present invention provides a method and apparatus for photoplethysmographic image analysis (PPGi) which allows oxygen saturation changes to be tracked with high accuracy over time using broadband lighting and standard RGB video cameras. Although not directly providing an absolute measure of oxygen saturation, the method of the invention accurately tracks changes in oxygen saturation and is robust to small movements of the subject and consistent over several hours of recording.

One aspect of the invention provides a method of determining changes in blood oxygen saturation of a subject comprising the steps of: obtaining a video image of an area of exposed skin of the subject, the video image comprising signals representing intensity in at least two different colour channels; defining in the image a plurality of regions of interest in said area of exposed skin of the subject; determining a signal to noise ratio of a heart rate or breathing rate frequency component of one of the colour channel signals for each region of interest; determining whether to reject or not reject regions of interest based on the determined signal to noise ratio of a heart rate or breathing rate frequency component or both; processing the colour channel signals from non-rejected regions of interest by: normalising the signal in each of the colour channels by dividing each of the signals by its baseline component; determining the ratio of the amplitudes of the normalised signals from two of the colour channel signals; and outputting changes over time in the ratio as representing changes in blood oxygen saturation of the subject.

The video image is preferably obtained using a standard RGB video camera such as a webcam, delivering a standard three colour channel (RGB) video signal.

Preferably the method further comprises the step of averaging each the normalised signals within each colour channel before calculating the ratio of amplitudes.

Preferably the processing steps of normalising and determining the ratio of amplitudes are performed on a series of overlapping temporal windows of the signal; for example each window can be 10-15 seconds long and moved for each processing cycle by 1-5 seconds. Thus a new measurement is output for every step, representing an average over the previous window length.

To normalise the signal in each of the colour channels, each signal is divided by its base line component, the baseline component being representative of the DC level of the signal in the window. For example the baseline component can be a temporal average over the window, for example the mean value of the signal over the window, or it could be a timeseries made up of the interpolated values of the per-pulse average or the troughs of the envelope of the signal. Preferably the two colour channel signals are the red and blue channels as the red channel is most affected by changes in oxygen saturation and the blue channel least affected, though the combination of green and red channels can be used.

Preferably the step of averaging each of the normalised signals comprises averaging together signals obtained from each of the plurality of regions of interest within the exposed area of the skin of the subject, thus providing spatial averaging. Thus an area of exposed skin of the subject may be found in the video image, for example by known techniques such as facial recognition, or recognising skin colour, or looking for areas of the image with a strong pulsatile component at the heart rate or in the physiologically possible range for heart rate, and the area is divided into the plural regions of interest which may be contiguous square or rectangular regions. One way of finding an area of exposed skin with a strong pulsatile component is to search for large areas where a signal to noise ratio function for the heart rate is maximised. This may be performed, for example, on the green channel of the RGB signal.

Preferably within each region of interest an estimate of the strength of the heart rate frequency component is obtained, for example by measuring the strength of the signal-to-noise ratio for a heart rate frequency component of one of the colour channels, and the contribution of the signal from that region to the average of the normalised signals is weighted according to the strength of the heart rate signal. The signal-to-noise ratio of the heart rate frequency component may be found in the red colour channel.

Preferably regions of interest are excluded from the determination if a number of conditions related to the heart rate frequency component, breathing rate frequency component and phase of the heart rate frequency component are met. Placing these conditions on inclusion helps in eliminating from the calculation regions of interest which are strongly affected by specular reflections. For example, a condition on the heart rate frequency component may be that its signal to noise ratio should exceed a predetermined threshold. A condition on the breathing rate frequency component may be that its signal to noise ratio is below a predetermined threshold (this allows the exclusion of regions which are affected by movement). Examining the phase of the heart rate frequency component, and in particular comparing the phase of the heart rate frequency component in the green channel from each region of interest with the phase of the heart rate frequency component averaged over all regions of interest additionally helps in excluding regions of interest which are affected by movement as the heart rate should be reasonably in phase (allowing for the pulse transit time) over a local area consisting of contiguous regions of interest.

Preferably, having obtained a normalised signal from the area of the exposed skin, the technique of signal averaging can be applied to determine a single representative waveform whose amplitude is then used in the ratio of ratios calculation. This is a self-referential time averaging technique. Preferably the signal averaging is performed by detecting a series of successive peaks in a time-windowed portion of the signal and selecting sections of the signal extending from a predetermined time before each peak to a predetermined time after it, and averaging together the selected sections. The section may extend from a time two thirds of the signal period before the peak to two thirds of the signal period after the peak, each section thus including slightly more than one signal period. This results in one average, representative waveform for the particular time-windowed portion of the signal. The amplitude of this waveform can be taken as representing the signal amplitude for that portion of signal.

Instead of spatially averaging the signals from the different regions of interest together, and then performing temporal signal averaging on the result to obtain a representative waveform, these steps may be reversed. Thus within each region of interest temporal signal averaging may be performed to obtain a representative waveform for each region of interest, and then representative waveforms from the different regions of interest can themselves be averaged together. Thus the techniques of spatial averaging over the different regions of interest and signal averaging within the time domain can be applied in either order.

The invention extends to a system or apparatus for determining changes in oxygen saturation of a subject, the system or apparatus including a video camera for obtaining the video image, a signal processor for performing the signal processing steps of the method and a display for outputting the changes over time in the ratio of amplitudes of the average normalised signals.

The signal processing steps of the invention may be applied to obtaining other vital signs measurements, such as heart rate and breathing rate, from RGB video images. Thus the effect of reflections and illumination changes can be reduced by including or rejecting regions of interest in the signal processing on the basis of the signal to noise ratio of a heart rate and/or breathing rate frequency component, and/or a phase comparison of a heart rate frequency signal from one region of interest with an average from all regions of interest.

Thus another aspect of the invention provides a method of determining a vital sign (such as heart rate or breathing rate) of a subject comprising the steps of: obtaining a video image of an area of exposed skin of the subject, the video image comprising signals representing intensity in at least two different colour channels; defining in the image a plurality of regions of interest in said area of exposed skin of the subject; determining a signal to noise ratio of a heart rate or breathing rate frequency component of one of the colour channel signals for each region of interest; determining whether to reject or not reject regions of interest based on the determined signal to noise ratio of a heart rate or breathing rate frequency component or both; processing the colour channel signals from non-rejected regions of interest to determine the vital sign. In addition to, or instead of, the rejection/non-rejection based on signal to noise ratio, a determination of whether to reject or not may be based on a phase comparison of a heart rate frequency signal from one region of interest with an average from all regions of interest.

This aspect of the invention also provides a corresponding apparatus for determining a vital sign (such as heart rate or breathing rate) of a subject, comprising a video camera for obtaining the video image, a signal processor for performing the signal processing steps of the method and a display for outputting the determined vital sign.

The method of the invention may be embodied in a computer program and the invention extends to such a computer program and to a computer readable medium carrying such a program.

The invention will be further described by way of example with reference to the accompanying drawings in which:—

Figure 3A:
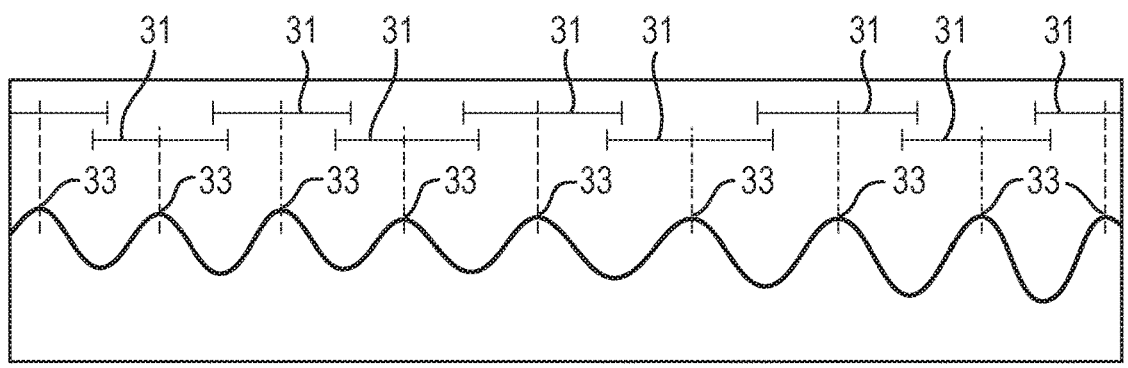
Figure 3B:
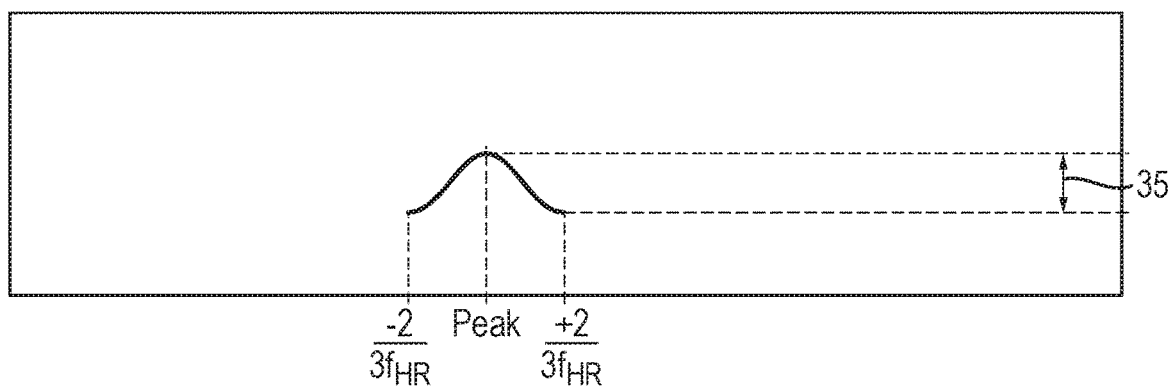
Figure 2:
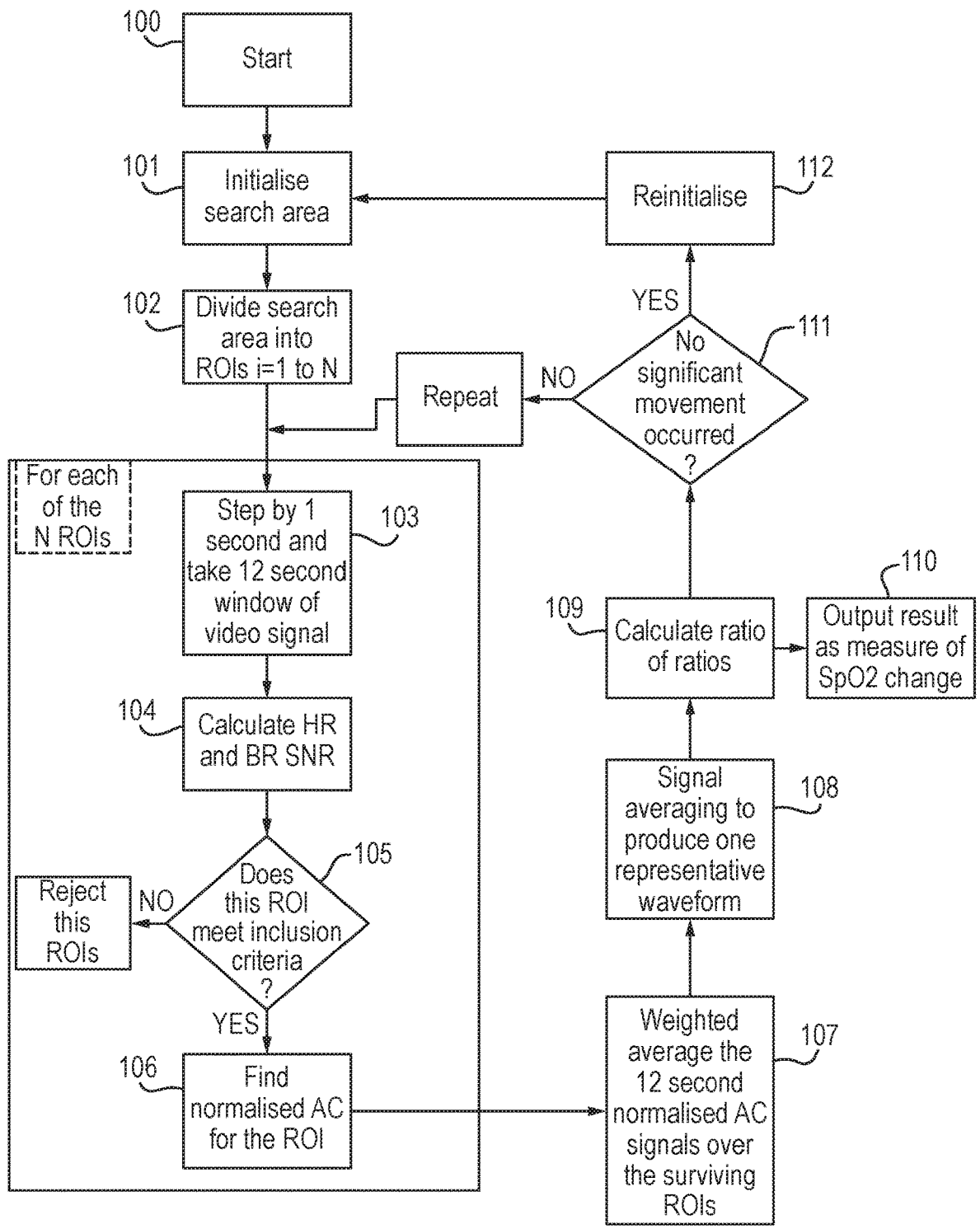

FIG. 1 schematically illustrates the system of the invention;

FIG. 2 is a flow diagram illustrating the steps of one embodiment of the invention;

FIGS. 3(a) and 3(b) schematically illustrate signal averaging; and

Figure 4A:
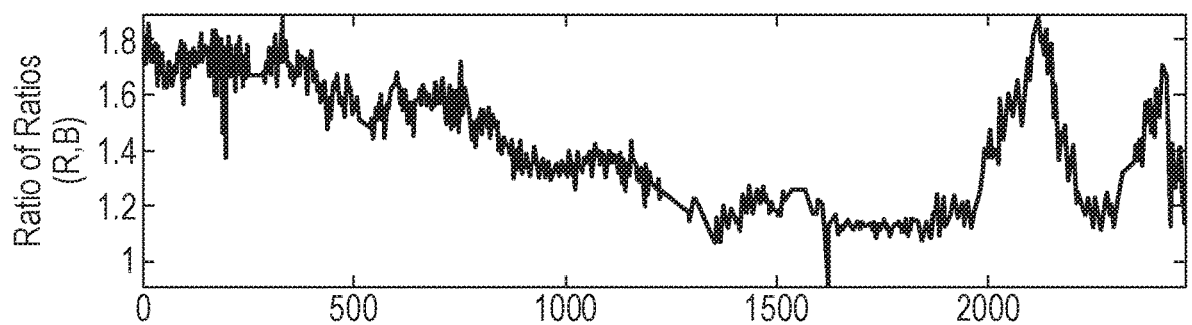
Figure 4B:
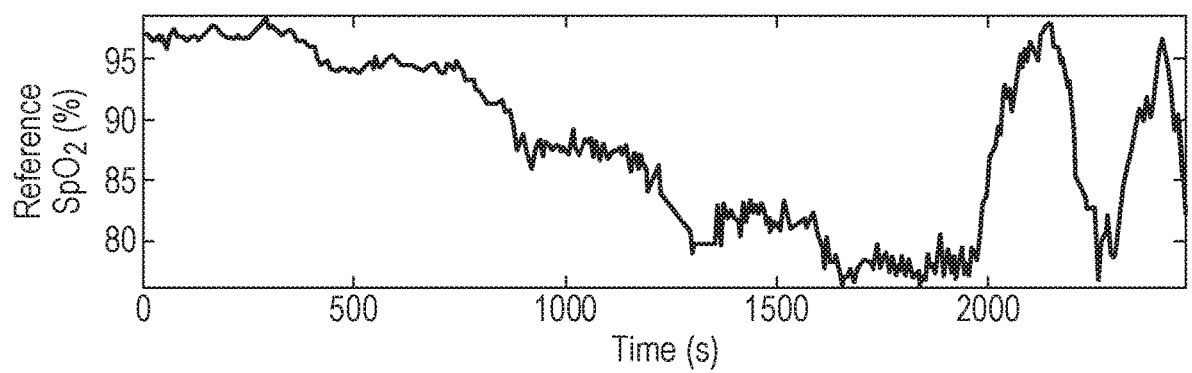

FIGS. 4(a) and 4(b) compare the results of monitoring oxygen saturation with an embodiment of the invention to results obtained using a finger-probe pulse oximeter.

In the context of broad-band illumination and the use of RGB sensors, the time-series $S_c^i$ of intensity values recorded by a camera from any given region of skin i for any given colour channel c may be decomposed into two parts: the baseline, or DC component, due to the residual blood present in the tissue at all times, and the pulsatile, heart-rate synchronous signal due to the change in colour as the blood flows in and out of the skin:

$$S_c^i(t) \propto DC_c^i(t) + AC_c^i(t) \qquad (1)$$

This assumes that all light is reflected diffusively and ignores any component due to specular reflection (we will see below that the signal processing used in the invention makes this a reasonable assumption). We will further assume that the whole timeseries $S_c^i(t)$ will be affected by only the following variable factors:

i) The intensity of the light reaching the skin at i
 ii) The vascular volume at i
 iii) The oxygen saturation.

Other factors that will affect the absorption of light in the skin, such as melanin, and the spectral distribution of the light source at i, are assumed to be constant. The method of the invention allows the elimination of the effects of light intensity and vascular volume changes so as to determine changes in oxygen saturation. Of the three factors i) to iii) above, the oxygen saturation is assumed to be locally-invariant, whereas the intensity of the light is allowed to vary locally (for example through geometrical effects such as shadowing), and the vascular volume is also allowed to vary locally (reflecting anatomical variation in the vasculature of the skin). Under these assumptions the relationship between the recorded intensity time series $S_c^i$ from a region i, the spectrally-invariant light intensity $I_c^i(t)$ reaching the region i, may be written as:

$$S_c^i(t) = I_c^i(t)[DC_c^i(t) + AC_c^i(t)] \qquad (2)$$

Using this model, the normalisation of the signal by the DC component will lead to an elimination of the effect of the local light intensity $I_c^i(t)$:

$$S_c^{i'}(t) = \frac{I_c^i(t)[DC_c^i(t) + AC_c^i(t)]}{I_c^i(t)DC_c^i(t)} \qquad (3)$$

$$= 1 + \frac{AC_c^i(t)}{DC_c^i(t)}$$

There are however other factors, such as local blood volume increases, that come into play with respect to the normalised AC component that are not necessarily eliminated by the normalisation itself. To eliminate these, the ratio of ratios $R^i(t)$ for two colour channels 1 and 2 is taken, under the assumption that all changes that are not due to oxygenation (and therefore cause a change in colour), will be proportional across the channels:

$$R^i(t) = \frac{s_1^{i'}(t) - 1}{s_2^{i'}(t) - 1} = \frac{\frac{k^i(t)AC_1^i(t)}{DC_1^i(t)}}{\frac{k^i(t)AC_2^i(t)}{DC_2^i(t)}} \qquad (4)$$

FIG. 1 schematically illustrates the system of the invention. A human (or animal) subject 1 is in the field of vision of an RGB video camera 3 whose three colour channel output is fed to a signal processor 5 and results are displayed on a display 7. The processor 5 identifies and analyses signals from one or more exposed areas of skin 10, 12 on the subject 1 and, as explained in more detail below, each of these exposed areas 10, 12 is itself divided into plural regions of interest.

The processing of the video signals by the processor 5 will be described with reference to the flowchart of FIG. 2.

Following starting of the processing at step 100, during an initialization step 101 an area of exposed skin is identified. This may be done either by applying specific prior knowledge about the scene (for example by face-detection if a face is known to be in the image), or by simply doing a search using a very large search area for the position at which the result of the SNR function for heart rate ($SNR_{HR}$) is maximised, where the SNR function is defined as:

$$SNR = SNR\{x(t)\}_a^b \qquad (5)$$

$$= 10\log\left(\frac{\int V|F\{x(t)\}|^2 df}{\int (1-V)|F\{x(t)\}|^2 df}\right)$$

for a detrended and appropriately filtered timeseries x(t), its Fourier transform $F\{x(t)\}$, and a double-step function $V(f)$ defined by the convolution:

$$V(f) = [\delta(f - \hat{f}) + \delta(f - 2\hat{f})] * \Pi(\pm f_h)$$

centred on the fundamental frequency of interest $\hat{f}$ and its first harmonic (e.g. $\hat{f} = \hat{f}_{HR}$ for heart rate), with δ as the Dirac delta function, and Π as the rect function of half-width $f_h$.

For the purpose of initialisation, x(t) is taken as the green signal over a period of 12 seconds, and the double-step function for the heart rate SNR is constructed with $f_{HR} = 1.4$ Hz and $f_h = 0.7$ Hz so as to cover the entire span of the expected physiological heart rate range.

Once a search area in which the totality of the skin to be image is included has been defined in step 102, the area is subdivided into N contiguous n by n pixel regions of interest i (n=40 for example). The size of the region of interest is set depending on the camera, lighting and physiology of the subject so that the region is as small as possible while still giving a detectable heart rate signal. Taking 12 second windows slid by 1 second at a time, crude estimates for the heart rate, $\hat{f}_{HR}$, and the breathing rate, $\hat{f}_{BR}$, are found. The heart rate estimate is found by taking the average of all the signals resulting from the per-frame spatial average of the green channel, then detrending and high-pass filtering this average prior to finding the peak of the Fourier Transform. The breathing rate estimate is instead found by taking the average of the power spectral density (PSD) of the detrended blue channel in the frequency domain across all regions of interest and then searching for a peak present in the expected physiological range (between 0.1 and 0.7 Hz corresponding to 6 to 42 breaths per minute). The differences in calculating the breathing rate and the heart rate are due to the fact that the relative phase shift between the heart rate signal, that is prevalently due to colour changes as a result of the inflow and outflow of blood during the cardiac cycle, estimated in two different regions of interest from the plurality of regions of interest, is uniquely determined by the pulse transit time between the two regions. The phase shift caused by the pulse transit time between the two regions is expected to be far smaller than π/2 radians. The breathing rate signals, on the other hand, are caused by changes in colour due to movement, and so can be either in phase or in antiphase as this will solely depend on the relative intensity of the pixels in the region of interest through time, and a temporal average would in fact minimise the breathing rate signal.

The spatial averages across the 12 second windows are then calculated for each of the channels of the N regions of interest i to reduce the three 2D plus time colour channel signals from each region to three 1D signals. The heart rate SNR function (5) as above is then applied to each of the N regions of interest using the red channel only and fixing the frequency limits a and b of the function at a=0.7 Hz and b=2.4 Hz, and $f_h$ is taken to be the quantisation limit of the FFT applied—e.g. 0.7 Hz. A breathing rate SNR function as defined in Equation 5 is also applied to each of the N regions of interest using the blue channel only and fixing the frequency limits a=0.1 Hz and b=0.7 Hz and the half-width of the breathing rate rect function $f_h$ is once more the quantisation limit of the FFT The results of the heart rate and breathing rate SNR functions serve to create a logical inclusion function $L^i$ that determines in step 105 whether the region of interest will be used in further calculations for that window or will be rejected. This serves to eliminate oscillations in the signal caused by specular reflections because the inclusion function serves to introduce a degree of confidence that the signal from the selected region of interest is from a colour change only. In fact, for a time series that contains only a pulsatility due to a true PPG skin colour change, we would expect a high result for the heart rate SNR, but a low result for the breathing rate SNR. This is because breathing rate is mostly associated with movement, and any region of interest that has a high breathing rate SNR will therefore have some component (whether a physical feature or a specular reflection) that is moving and thus does not fit the model's assumptions. In addition to this, a further condition is imposed: the heart rate component of the green channel of the region interest needs to be in phase with the green heart rate signal derived for the whole search area. This condition stems from the understanding that only movement-induced pulsations can be in phase or antiphase, and is determined by meeting the condition $p^i=1$ where:

$$p^i = \begin{cases} 1, & \text{if } |\phi_g^i(\hat{f}_{HR}) - \phi_G(\hat{f}_{HR})| < \frac{\pi}{2} \\ 0, & \text{otherwise} \end{cases}$$

where $\phi_g^i(\hat{f}_{HR})$ is the phase of the heart rate frequency component of the green signal of the region of interest i considered, and $\phi_G(\hat{f}_{HR})$ is the phase of the heart rate frequency component of the green signal averaged over the entire area. A phase difference of $\pi/2$ is chosen here because this gives the clearest demarcation between phase estimates that can be said to be in phase (but for a phase shift caused by a delay due to the pulse transit time) and the case for which two phase estimates are exactly in antiphase. The overall logical inclusion function is then given by:

$$L^i = (SNR_{HR}^i > SNR_{HR}^{thresh}) \cap (SNR_{BR}^i < SNR_{BR}^{thresh}) \cap p^i$$

with $SNR_{HR}^{thresh}$ and $SNR_{BR}^{thresh}$ determined by the initial conditions of the video (these will depend on skin colour, light intensity, light spectrum and distance from the camera). The thresholds can, for example, be taken as the mean plus one standard deviation of the SNRs in each of the regions of interest over the first stable window. In Step 106, the normalised amplitude is determined for each colour channel as per Equation 4 in all M regions of interest that meet the condition $L^i=1$. As the method depends on multiple regions to reduce the measurement error, a minimum number of regions M≥3 is set at each iteration or the window is rejected. The DC component is taken as the time-average of the window for each colour channel and each region of interest individually and the AC component is taken to be the residual of the original timeseries after the DC component has been subtracted out. A weighted average of all the M normalised amplitudes is then taken in step 107 for each of the channels, in which the region of interest weightings $\omega_i$ are a function of the heart rate SNR, such that:

$$\omega_i = \frac{SRN_{HR}^j}{\sum^M SNR_{HR}^i}, \{i: L^j = 1\}$$

The weighting introduces an additional degree of belief in each region of interest, favouring regions of interest that have a high heart rate signal-to-noise ratio as these are more likely to correspond to the ideal surfaces that are considered in the theoretical model.

Finally, in step 108 a self-referential signal averaging procedure is applied to the averaged waveforms. This is done by taking the green channel averaged waveform, high-pass filtering it and finding the positions of the peaks in the waveform (the green channel is used because it has a high signal-to-noise ratio). In each of the three colour channels all samples around the peaks $$\pm \frac{2}{3f_{HR}}$$

in the averaged waveforms are then averaged together to obtain a single representative waveform for the entire 12-second period for each channel. The amplitude of the waveform is taken as the normalised amplitude for that channel and the ratio of the blue normalised amplitude with respect to the normalised amplitude of the red channel is then taken as the ratio of ratios in step 109. The ratio of the normalised blue amplitude divided by the normalised red amplitude emerging from step 109, or its logarithm, is then output in step 110 as representative of the oxygen saturation and displayed on display 7. Steps 103 to 110 are then repeated until there is a significant movement of the subject outside of the search area as checked at step 111, at which point the algorithm is halted until there is a period of no movement and then reinitialised in step 112 and restarted.

FIGS. 3(a) and (b) schematically illustrate a signal averaging process applied to a waveform from one colour channel. In FIG. 3(a), sections 31 of each of the successive waveforms centred on the peaks 33 are taken, the peaks are aligned and the waveforms averaged to produce a single representative shape waveform for that signal as shown in FIG. 3(b). The amplitude 35 of the representative waveform is taken as the amplitude for that signal.

Although in FIG. 2 and as explained above, the 12-second sections of signal are first averaged over all regions of interest in step 107, and then signal averaging within the 12-second section is performed on the result in step 108, these steps can be performed the other way around. Thus signal averaging for each 12-second section can be conducted for each region of interest to produce a single representative waveform for each region of interest. Then the representative waveforms from the plural regions of interest can be averaged to produce a final representative waveform and corresponding amplitude for that 12-second section of signal.

FIG. 4 illustrates results obtained (log of the ratio of ratios of the normalised blue signal to the normalised red signal) by tracking a volunteer's oxygen saturation in accordance with the invention and simultaneously using a standard finger-probe pulse oximeter. A 3-CCD (JAIAT-200CL) RGB camera was used and the volunteer was placed in a study chamber in which the relative concentrations of oxygen, carbon dioxide, and nitrogen could be modified so as to induce mild hypoxia and hypercapnia. To produce the results of FIG. 4 the oxygen concentrations of the chamber were modified by changing the concentration of nitrogen in accordance with the following protocol: the concentrations were lowered so as to induce a change in oxygen saturation in steps of five percent (as measured by the reference pulse oximeter) each lasting seven minutes, from base line oxygen saturation (around 97 percent) to 80 percent. Two cycles of fast re-saturations and de-saturations then took place through the use of a nasal cannula for oxygen delivery.

As can be seen, the changes in oxygen saturation as measured by the method of the invention using the video camera shown in FIG. 4(a) track the changes in oxygen saturation measured by the reference pulse oximeter in FIG. 4(b) reasonably well.

As mentioned above the calculation made by the invention does not directly result in an oxygen saturation value. However in a clinical setting oxygen saturation values may be obtained by first calibrating the system using a standard pulse oximeter. Thus a subject's oxygen saturation can be measured initially (and potentially at intervals thereafter) using a standard finger-probe pulse oximeter, with this value being used to calibrate the system of the invention, the method of the invention then being used primarily to track variations from that initial saturation. Significant decreases in oxygen saturation, which might represent a worsening of the subject's condition, can be used to trigger an alarm to the clinicians.

Although the main thrust of the invention is to track changes in oxygen saturation, the estimated heart rate and breathing rate used in the method can be output and displayed on display 7 as additional vital signs information.

The invention claimed is:

1. A method of determining changes in blood oxygen saturation of a subject comprising the steps of:
    obtaining a video image of an area of exposed skin of the subject, the video image comprising signals representing intensity in at least two different colour channels;
    defining in the image a plurality of regions of interest in said area of exposed skin of the subject;
    determining a signal to noise ratio of a heart rate or breathing rate frequency component of one of the colour channel signals or both for each region of interest;
    determining whether to reject or not reject regions of interest based on the determined signal to noise ratio of a heart rate or breathing rate frequency component or both;
    processing the colour channel signals from non-rejected regions of interest by:
        normalising the signal in each of the colour channels by dividing each of the signals by its baseline component;
        determining the ratio of the amplitudes of the normalised signals from two of the colour channel signals; and
    outputting changes over time in the ratio as representing changes in blood oxygen saturation of the subject.

2. The method according to claim 1 wherein the baseline component is the average value of the signal over a predetermined period.

3. The method according to claim 1 wherein the ratio of the amplitudes of the averaged normalised signals from blue and red colour channel signals are determined.

4. The method according to claim 1 further comprising the step of averaging each the normalised signals within each colour channel before calculating the ratio of amplitudes.

5. The method according to claim 4 wherein the step of averaging each of the normalised signals within each colour channel comprises averaging together the signals for that colour channel from each of a plurality of regions of interest within said area of skin of the subject.

6. The method according to claim 5 wherein in averaging each of the normalised signals within each colour channel the signals from each region of interest are weighted according to the strength of the signal to noise ratio for a heart rate frequency component of one of the colour channel signals from that region of interest.

7. The method according to claim 4 wherein the step of averaging each of the normalised signals within each colour channel comprises signal averaging to determine a representative waveform for a predetermined time period of said signal.

8. The method according to claim 7 wherein said signal averaging comprises detecting the times of peaks in one of the colour channel signals, then within each colour channel selecting sections of the normalised signal extending a predetermined time either side of the detected peak times and averaging together the selected sections of the normalised signal.

9. The method according to claim 1 wherein the area of exposed skin of the subject is selected by detecting areas in the image for which a signal to noise ratio function for the heart rate is maximised.

10. The method according to claim 1 wherein the regions of interest are formed by dividing the selected area into plural contiguous regions.

11. The method according to claim 1 wherein regions of interest are rejected if a signal to noise ratio for a heart rate frequency component of a colour channel signal from the region of interest is below a predetermined threshold.

12. The method according to claim 1 wherein regions of interest are rejected if a signal to noise ratio for a breathing rate frequency component of a colour channel signal from the region of interest is above a predetermined threshold.

13. The method according to claim 1 wherein regions of interest are rejected if the phase of a heart rate frequency component of a colour channel signal from the region of interest is outside a predetermined threshold of the phase of a heart rate frequency component of the colour channel signal averaged over a plurality of the regions of interest.

14. The method according to claim 1 wherein the signal in each colour channel is windowed into temporal windows, and the processing steps of normalising and determining are performed for each time window to determine and output a ratio for each time window.

15. A system for determining changes in blood oxygen saturation of a subject comprising:
    a video camera for obtaining a video image of an area of exposed skin of the subject, the video image comprising signals representing intensity in at least two different colour channels;
    a signal processor adapted to receive the signals from the video camera and process them by:

normalising the signal in each of the colour channels by dividing each of the signals by its baseline component;

defining in the image a plurality of regions of interest in said area of exposed skin of the subject;

determining a signal to noise ratio of a heart rate or breathing rate frequency component of one of the colour channel signals or both for each region of interest;

determining whether to reject or not reject regions of interest based on the determined signal to noise ratio of a heart rate or breathing rate frequency component or both;

determining the ratio of the amplitudes of the normalised signals from two of the colour channel signals for non-rejected regions of interest; and outputting changes over time in the ratio as representing changes in blood oxygen saturation of the subject; and a display adapted to display the changes over time in the ratio.

* * * * *